(12) United States Patent
Eddy

(10) Patent No.: US 8,491,922 B2
(45) Date of Patent: Jul. 23, 2013

(54) ANTIMICROBIAL ISOPROPYL ALCOHOL AND ORGANOFUNCTIONAL SILANE SOLUTION

(75) Inventor: Patrick E. Eddy, Allendale, MI (US)

(73) Assignee: MicrobeCare, LLC, Albany, GA (US)

( * ) Notice: Subject to any disclaimer, the term of this patent is extended or adjusted under 35 U.S.C. 154(b) by 26 days.

(21) Appl. No.: 13/182,657

(22) Filed: Jul. 14, 2011

(65) Prior Publication Data

US 2012/0052106 A1    Mar. 1, 2012

Related U.S. Application Data

(60) Provisional application No. 61/376,481, filed on Aug. 24, 2010.

(51) Int. Cl.
*A01N 25/02* (2006.01)

(52) U.S. Cl.
USPC .......................................................... 424/405

(58) Field of Classification Search
None
See application file for complete search history.

(56) References Cited

U.S. PATENT DOCUMENTS

| | | | |
|---|---|---|---|
| 5,079,004 A * | 1/1992 | Blank et al. | 424/404 |
| 7,045,673 B1 | 5/2006 | Batich et al. | |
| 7,709,694 B2 | 5/2010 | Batich et al. | |
| 7,790,217 B2 | 9/2010 | Toreki et al. | |
| 2007/0042198 A1 | 2/2007 | Schonemyr et al. | |

OTHER PUBLICATIONS http://www.igenericdrugs.com/?s=Life%20Brand%20Disinfectant%20Wipes, 2012.*
http://www.zorotools.com/g/Respirator%20Antimicrobial%20Wipes/00118290, 2012/.*
http://www.ncbi.nlm.nih.gov/pubmed/7753434, 1995.*
Sickbert-Bennett, "Comparative Efficacy of Hand Hygiene Agents in the Reductions of Bacteria and Viruses", Association for Professionals in Infection Control and Epidemiology, Inc. 2005.*
"Graft Polymerization onto Wool Pretreated with a Mercaptosilane", Textile Research Journal, Aug. 1996, vol. 66, No. 6, 529-532.*

* cited by examiner

*Primary Examiner* — Carlos Azpuru
(74) *Attorney, Agent, or Firm* — Price Henevled LLP

(57) ABSTRACT

A surface of an object may be treated using an antimicrobial wipe presoaked in an antimicrobial treatment solution. Alternatively, the antimicrobial treatment solution may be sprayed directly on the surface. The antimicrobial treatment solution may be made of isopropyl alcohol and an unreacted organofunctional silane antimicrobial substance that is substantially free from arsenic, silver, tin, heavy metals and polychlorinated phenols. The antimicrobial substance may include any one of: 3 trimethoxysilylpropyloctadecyldimethyl ammonium chloride; hyaluronan and its derivatives; triclosan; and a copolymer of chloropropyltrihydroxysilane and octadecylaminodimethyltrihydroxysilylpropyl ammonium chloride.

18 Claims, 3 Drawing Sheets

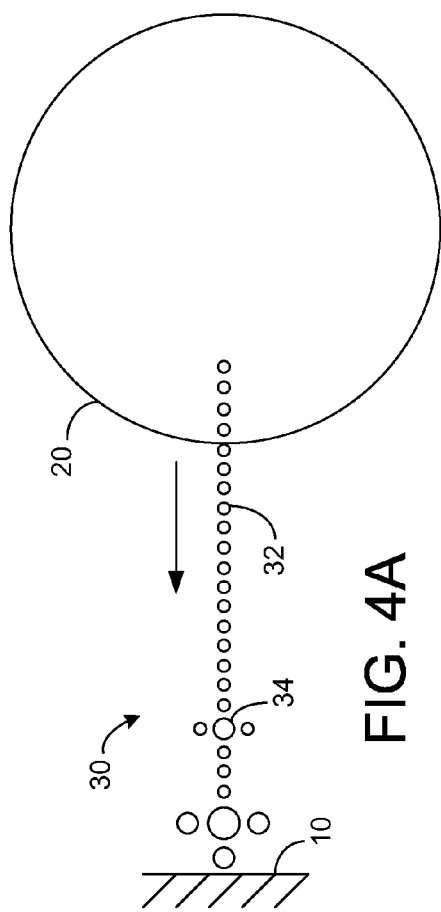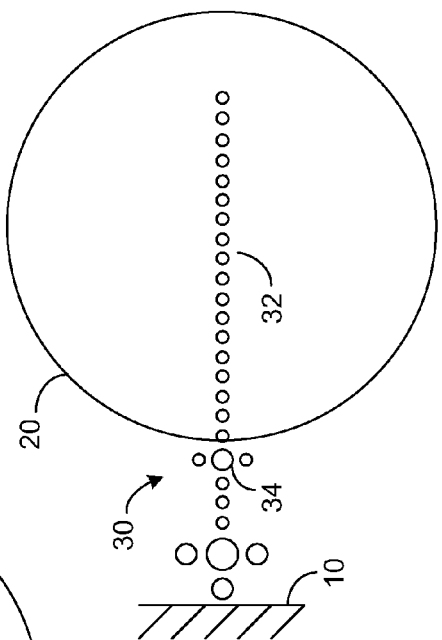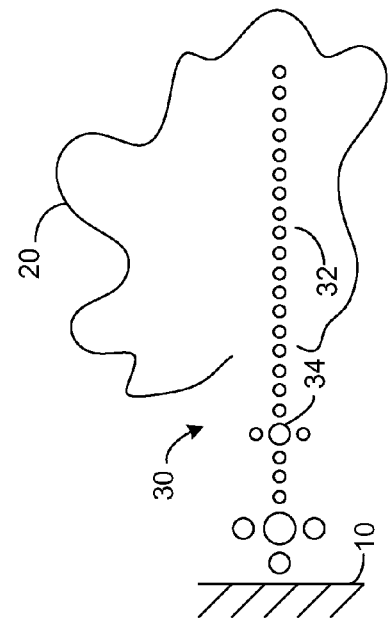

ANTIMICROBIAL ISOPROPYL ALCOHOL AND ORGANOFUNCTIONAL SILANE SOLUTION

CROSS-REFERENCE TO RELATED APPLICATIONS

This application claims priority under 35 U.S.C. §119(e) upon U.S. Provisional Patent Application No. 61/376,481, entitled "ANTIMICROBIAL WIPES" filed on Aug. 24, 2010, by Patrick E. Eddy, the entire disclosure of which is incorporated herein by reference.

BACKGROUND OF THE INVENTION

Disposable wipes that are wetted in various solutions for general cleaning and/or disinfecting are currently available in the marketplace. People use these wipes on themselves or others and use them on various items to be cleaned and disinfected. While such wipes are useful in killing any bacteria present on the item that is wiped, they do not prevent bacteria from subsequently collecting on the item that was wiped, and thus do not "treat" the surface of the item.

Published U.S. Patent Application Publication No. 2007/0042198 A1 discloses an antimicrobial substrate and a method and composition for producing it. This publication discloses that the substrate may take many different forms including that of a wipe. As explained further below, such a wipe uses a "reacted" organosilicon antimicrobial substance and thus is not useful for treating a surface of an item.

SUMMARY OF THE INVENTION

According to an embodiment of the present invention, an antimicrobial wipe is provided comprising: an antimicrobial treatment solution comprising an unreacted organofunctional silane antimicrobial treatment substance that is substantially free from arsenic, silver, tin, heavy metals and polychlorinated phenols; and a wiping substrate stored within the antimicrobial treatment solution.

According to an embodiment of the present invention, an antimicrobial treatment solution comprises isopropyl alcohol and an unreacted organofunctional silane antimicrobial treatment substance that is substantially free from arsenic, silver, tin, heavy metals and polychlorinated phenols.

According to an embodiment of the present invention, a method of treating a surface with an antimicrobial treatment solution comprises the steps of: providing an antimicrobial treatment solution comprising isopropyl alcohol and an unreacted organofunctional silane antimicrobial treatment substance that is substantially free from arsenic, silver, tin, heavy metals and polychlorinated phenols; and applying the antimicrobial treatment solution to the surface to be treated. The step of applying the antimicrobial treatment solution to the surface may include spraying the antimicrobial treatment solution onto the surface and/or providing a wipe soaked in the antimicrobial treatment solution and using the wipe to transfer the solution to the surface.

These and other features, advantages, and objects of the present invention will be further understood and appreciated by those skilled in the art by reference to the following specification, claims, and appended drawings.

BRIEF DESCRIPTION OF THE DRAWINGS

In the drawings:

FIG. 4A is a schematic representation of the monomer shown in FIGS. 2 and 3 illustrating a first step in the manner by which the monomer destroys a microbe;

FIG. 4B is a schematic representation of the monomer shown in FIGS. 2 and 3 illustrating a second step in the manner by which the monomer destroys a microbe; and FIG. 4C is a schematic representation of the monomer shown in FIGS. 2 and 3 illustrating a third step in the manner by which the monomer destroys a microbe.

DETAILED DESCRIPTION OF PREFERRED EMBODIMENTS

Figure 1:
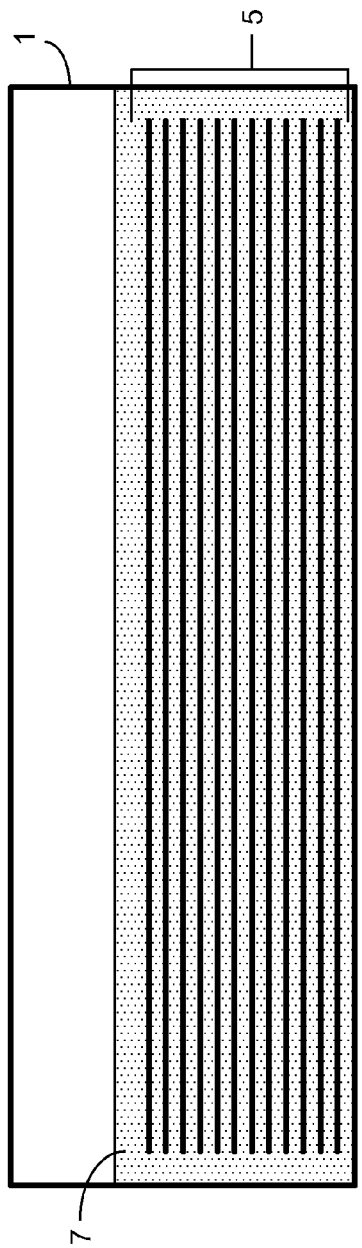
FIG. 1 is a cross-sectional view of a container containing wipes and an antimicrobial treatment solution in accordance with an embodiment of the present invention.

Reference will now be made in detail to the present preferred embodiments of the invention, examples of which are illustrated in the accompanying drawings. Wherever possible, the same reference numerals will be used throughout the drawings to refer to the same or like parts. In the drawings, the depicted structural elements are not to scale and certain components are enlarged relative to the other components for purposes of emphasis and understanding.

A novel wipe and novel wetting solution for wipes are disclosed herein that not only eliminate bacteria on contact, but which also provide an antimicrobial treatment for the item being wiped. Such anti-bacterial treatment remains on the treated item and kills any bacteria subsequently contacting the item. Such treatment preferably lasts at least one week, more preferably several months, and most preferably indefinitely.

Conventional wipes are typically packaged by providing a plurality of folded and stacked wipe substrates in a package in which a wiping solution is applied to soak the wiping substrates. Conventional wiping solutions have been known to have been composed of 70 percent isopropyl alcohol and 30 percent water. In accordance with the present invention, a percentage of the isopropyl alcohol and/or water is replaced with one of the antimicrobial treatment substances described below to provide an antimicrobial treatment solution.

FIG. 1 shows an example of an embodiment wherein a container 1 includes a plurality of wipe substrates 5 soaking in an antimicrobial treatment solution 7. The wipe substrates 5 may be formed of synthetic non-wovens, cotton blend non-wovens, and other suitable materials.

The antimicrobial treatment substance may include Microguard® (by Microguard, Olivet, France), which is a liquid solution containing hydrophilic polymers; Microban® antimicrobial additive available from Microban International; AEGIS Microbe Shield™ (from Aegis Environments, Midland, Mich.), which is a copolymer of chloropropyltrihydroxysilane and octadecylaminodimethyltrihydroxysilylpropyl ammonium chloride; 3 trimethoxysilylpropyloctadecyldimethyl ammonium chloride; hyaluronan and its derivatives; triclosan; an organofunctional silane antimicrobial treatment substance that is substantially free from arsenic, silver, tin, heavy metals and polychlorinated phenols; copper; or a silver-ion emitter. One silver-ion emitter is Germ-Gate™ (from Bovie Screen Process Co., Inc., Bow, N.H.), which is a nano particle silver-based liquid coating that can be coated onto a fabric. Another silver-ion emitter is Protex$^{AG}$ (from Carolina Silver Technologies, N.C.), which is a silver-based coating that can be coated onto fabric. Yet other silver-ion emitting coatings are those available from Covalon Technologies, Ltd. of Mississauga, Ontario, Canada; Agion® antimicrobial coating available from Agion Technologies Ltd. of Wakefield, Mass.; and Zeolite carrying silver, Model No. XDK101 available from Xiamen Xindakang Inorganic Materials Co., Ltd. In addition, silver sodium hydrogen zirconium phosphate may be used as the antimicrobial treatment substance. Alternate antimicrobial substances may be used that are tolerant of appropriate cleaning and sterility methods. An example of which is zirconium phosphate such as Model No. XDK801 available from Xiamen Xindakang Inorganic Materials Co., Ltd. In general terms, an antimicrobial treatment substance is capable of emitting ions that aid in the destruction of a microbe.

In a preferred form, the antimicrobial treatment wiping solution contains 30-50 percent isopropyl alcohol and 50-70 percent antimicrobial treatment substance, which is preferably an unreacted organofunctional silane including a copolymer of chloropropyltrihydroxysilane and octadecylaminodimethyltrihydroxysilylpropyl ammonium chloride, such as that available from Aegis Environments, Midland, Mich., under the trademark AEGIS Microbe Shield™. The isopropyl alcohol has a concentration of 70-90 percent. By providing the unreacted organofunctional silane in isopropyl alcohol, the organofunctional silane does not react with the wipe substrates or the inside of the container such that it is free to later react and permanently covalently bond with the surface to be treated. Isopropyl alcohol is preferred as it evaporates quickly once the solution is wiped onto the treated surface to allow the unreacted organofunctional silane to more quickly react with the treated surface. If the organofunctional silane is in its reacted form so as to permanently bond to the wipes, as in the case disclosed in U.S. Patent Application Publication No. 2007/0042198 A1, it cannot then bond to another surface and cannot "treat" that surface to prevent future microbe contamination.

Figure 2:
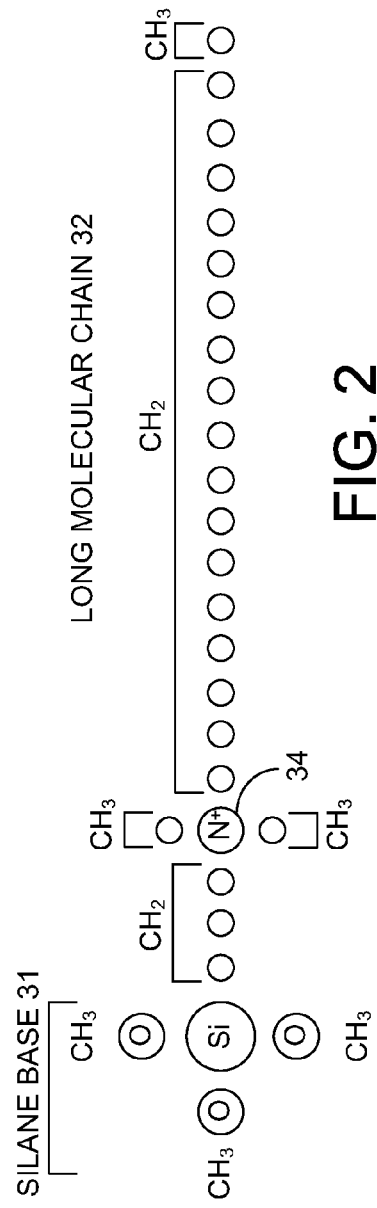
FIG. 2 is a schematic representation of a monomer that may be used in the embodiments described herein as an antimicrobial treatment substance.
Figure 3:
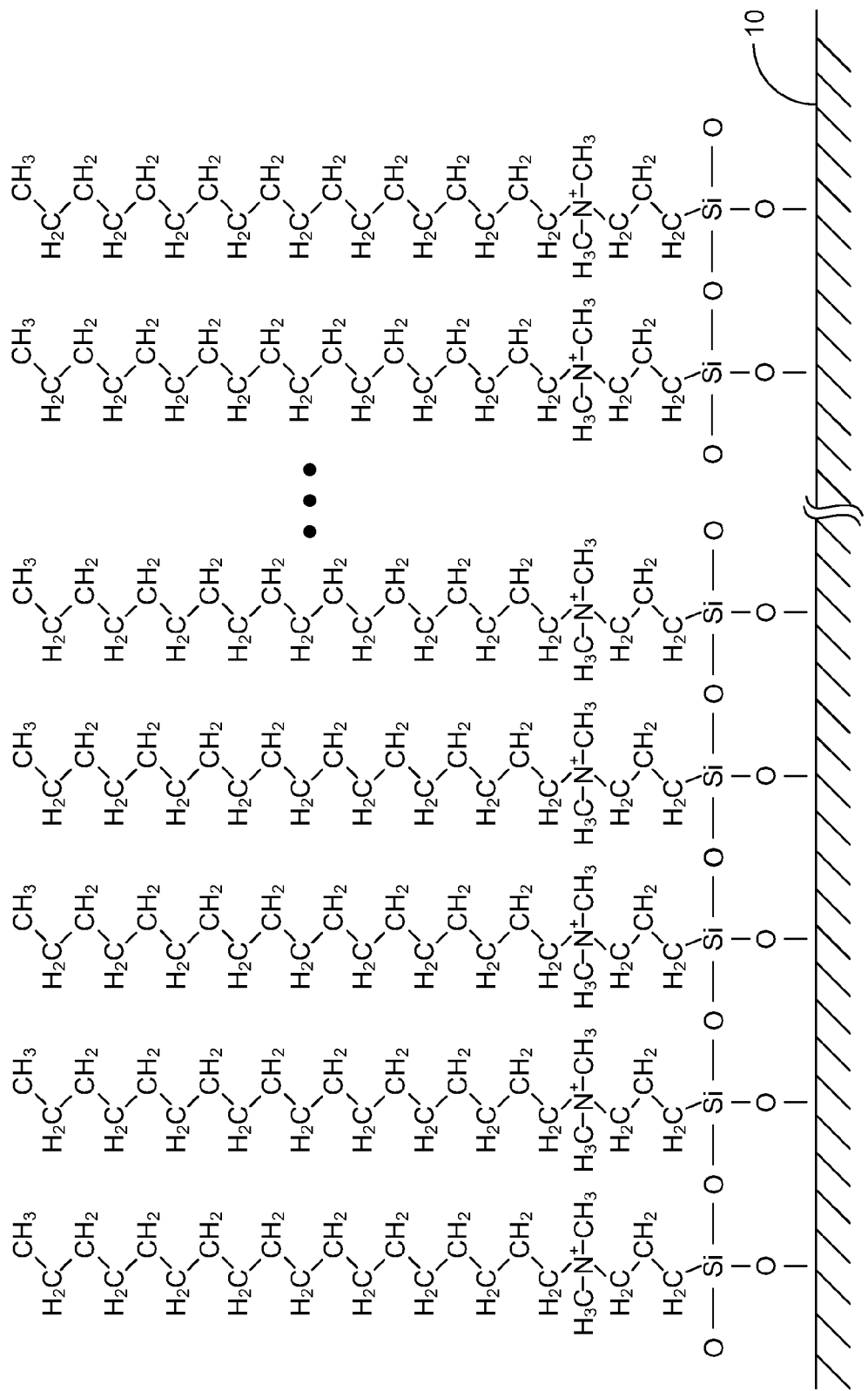
FIG. 3 is a schematic representation of a plurality of the monomers shown in FIG. 2 as applied to a treated surface.

FIG. 2 shows a schematic representation of a monomer form 30 of a preferred organofunctional silane. As illustrated, monomer 30 includes a silane base 31 for bonding to a surface, a positively charged nitrogen molecule 34, and a long molecular chain 32. As shown in FIG. 3, the silane bases of these monomers covalently and permanently bond to each other and to the surface 10 to be treated in such a way that the long molecular chains are aligned and pointing outward from the surface 10. This tight bonding provides a micropolymer network that serves as a protective coating on the outside of the surface 10 that destroys any microbes that come into contact.

The manner by which the preferred organofunctional silane destroys microbes is illustrated in FIGS. 4A-4C. Such microbes may include bacteria, mold, mildew, algae, etc. As shown in FIG. 4A, the cell membrane 20 of the microbe is attracted to the treated surface 10 and then is punctured by the long molecular chain 32 of the monomer 30. As the microbe is drawn closer because of the positive-negative ion exchange, the monomer 30 penetrates further into the cell membrane 20 as shown in FIG. 4B. Once the cell membrane 20 is penetrated deeply, it is physically ruptured by a swordlike action and then electrocuted by a positively charged nitrogen molecule 34 of the monomer 30, thus destroying the microbe as illustrated in FIG. 4C. Thus, the microbes are eliminated without "using up" any of the antimicrobial active ingredient, which remains on the surface ready to continue protecting the treated item against further microbial contamination.

The preferred organofunctional silane also prevents odor, staining and product deterioration that may be associated with microbe contamination. The preferred organofunctional silane is also beneficial because it permanently bonds to a treated surface, covers a broad spectrum of activity with no negative effects or drawbacks and is easily incorporated and easily verifiable.

The preferred organofunctional silane is designed to react and create a covalant bond with the surface to which it is applied. The reacted substance is held onto that surface until the covalant bond is broken. Tests have shown that most industrial cleaners or disinfectants will not remove the preferred organofunctional silane antimicrobial treatment substance. The method of removal is by abrasion.

A novel method of treating a surface of a medical device and other items used in a medical setting is provided by the ability to use the inventive wipes to wipe down such a surface in order to provide a treatment to the surface such that it will thereafter act as an antimicrobial surface. In broader terms, the method of treating a surface with an antimicrobial treatment solution may comprise the steps of: providing an antimicrobial treatment solution comprising isopropyl alcohol and unreacted organofunctional silane antimicrobial treatment substance that is substantially free from arsenic, silver, tin, heavy metals and polychlorinated phenols; and applying the antimicrobial treatment solution to the surface to be treated. The step of applying the antimicrobial treatment solution to the surface may include spraying the antimicrobial treatment solution onto the surface and/or providing a wipe soaked in the antimicrobial treatment solution and using the wipe to transfer the solution to the surface.

If the antimicrobial treatment solution is applied by spraying, the solution most preferably includes 50 percent isopropyl alcohol and 50 percent of the unreacted antimicrobial treatment substance. If the solution is applied using the wipes, the solution is preferably 30 percent isopropyl alcohol and 70 percent of the unreacted antimicrobial treatment substance.

The above description is considered that of the preferred embodiments only. Modifications of the invention will occur to those skilled in the art and to those who make or use the invention. Therefore, it is understood that the embodiments shown in the drawings and described above are merely for illustrative purposes and not intended to limit the scope of the invention, which is defined by the following claims as interpreted according to the principles of patent law, including the doctrine of equivalents.

I claim:

1. An antimicrobial treatment solution comprising an isopropyl alcohol and an unreacted organofunctional silane antimicrobial treatment substance that is substantially free from arsenic, silver, tin, heavy metals and polychlorinated phenols.

2. An antimicrobial wipe comprising:
   the antimicrobial treatment solution of claim 1; and
   a wiping substrate stored within the antimicrobial treatment solution.

3. The antimicrobial wipe of claim 2, wherein the antimicrobial treatment substance comprises 3 trimethoxysilylpropyloctadecyldimethyl ammonium chloride.

4. The antimicrobial wipe of claim 2, wherein the antimicrobial treatment substance is capable of emitting ions that aid in the destruction of a microbe.

5. The antimicrobial wipe of claim 2, wherein the antimicrobial treatment solution further comprises isopropyl alcohol.

6. The antimicrobial wipe of claim 5, wherein the antimicrobial treatment solution comprises about 30 percent to about 50 percent of isopropyl alcohol.

7. The antimicrobial wipe of claim 2, wherein the antimicrobial treatment substance comprises any one of: 3 trimethoxysilylpropyloctadecyldimethyl ammonium chloride;

triclosan; and a copolymer of chloropropyltrihydroxysilane and octadecylaminodimethyltrihydroxysilylpropyl ammonium chloride.

8. The antimicrobial treatment solution of claim 1, wherein the antimicrobial treatment substance comprises any one of: 3 trimethoxysilylpropyloctadecyldimethyl ammonium chloride; triclosan; and a copolymer of chloropropyltrihydroxysilane and octadecylaminodimethyltrihydroxysilylpropyl ammonium chloride.

9. The antimicrobial treatment solution of claim 1, wherein the antimicrobial treatment substance comprises 3 trimethoxysilylpropyloctadecyldimethyl ammonium chloride.

10. The antimicrobial treatment solution of claim 1, wherein the antimicrobial treatment substance is capable of emitting ions that aid in the destruction of a microbe.

11. The antimicrobial treatment solution of claim 1, wherein the antimicrobial treatment solution comprises about 30 percent to about 50 percent of isopropyl alcohol.

12. A method of treating a surface with an antimicrobial treatment solution comprising the steps of:
provulating the antimicrobial treatment solution of claim 1; and
applying the antimicrobial treatment solution to the surface to be treated.

13. The method of claim 12, wherein the step of applying the antimicrobial treatment solution to the surface includes spraying the antimicrobial treatment solution onto the surface.

14. The method of claim 12, wherein the step of applying the antimicrobial treatment solution to the surface includes providing a wipe soaked in the antimicrobial treatment solution and using the wipe to transfer the antimicrobial treatment solution to the surface.

15. The method of claim 12, wherein the antimicrobial treatment substance comprises any one of: 3 trimethoxysilylpropyloctadecyldimethyl ammonium chloride; triclosan; and a copolymer of chloropropyltrihydroxysilane and octadecylaminodimethyltrihydroxysilylpropyl ammonium chloride.

16. The method of claim 12, wherein the antimicrobial treatment substance comprises 3 trimethoxysilylpropyloctadecyldimethyl ammonium chloride.

17. The method of claim 12, wherein the antimicrobial treatment solution comprises about 30 percent to about 50 percent of isopropyl alcohol.

18. The method of claim 12, wherein upon applying the antimicrobial treatment solution, an antimicrobial coating is formed on the surface by forming covalent bonds between the antimicrobial treatment solution and the surface to be treated.

* * * * *